US010673922B2

(12) United States Patent
Golay (10) Patent No.: US 10,673,922 B2
(45) Date of Patent: Jun. 2, 2020

(54) CLOUD BASED 2D DENTAL IMAGING SYSTEM WITH HTML WEB BROWSER ACQUISITION

(71) Applicant: Douglas A. Golay, Coon Rapids, IA (US)

(72) Inventor: Douglas A. Golay, Coon Rapids, IA (US)

(73) Assignee: RealCloud Imaging Inc., Ames, IA (US)

( * ) Notice: Subject to any disclaimer, the term of this patent is extended or adjusted under 35 U.S.C. 154(b) by 180 days.

(21) Appl. No.: 14/184,477

(22) Filed: Feb. 19, 2014

(65) Prior Publication Data

US 2015/0237106 A1      Aug. 20, 2015

(51) Int. Cl.
| | |
|---|---|
| *H04L 29/08* | (2006.01) |
| *A61B 6/14* | (2006.01) |
| *G01T 1/16* | (2006.01) |
| *H04L 29/06* | (2006.01) |
| *G06F 19/00* | (2018.01) |
| *H04N 5/32* | (2006.01) |
| *A61B 6/00* | (2006.01) |
| *H04N 5/232* | (2006.01) |
| *H04N 5/225* | (2006.01) |

(52) U.S. Cl.
CPC .............. *H04L 67/02* (2013.01); *A61B 6/145* (2013.01); *A61B 6/563* (2013.01); *G06F 19/321* (2013.01); *H04N 5/23206* (2013.01); *H04N 5/32* (2013.01); *H04N 2005/2255* (2013.01)

(58) Field of Classification Search
CPC ......... H04L 67/02; A61B 6/145; A61B 6/563; G06F 19/321; H04N 5/23206; H04N 5/32; H04N 2005/2255
See application file for complete search history.

(56) References Cited

U.S. PATENT DOCUMENTS

| | | | | |
|---|---|---|---|---|
| 2005/0144222 A1* | 6/2005 | Marshall | ............ | A61C 13/0004 709/203 |
| 2012/0027256 A1* | 2/2012 | Kiyohara | .......... | G06F 17/30029 382/103 |
| 2012/0189182 A1* | 7/2012 | Liang | ..................... | A61C 19/00 382/131 |

(Continued)

*Primary Examiner* — Abdullahi E Salad
(74) *Attorney, Agent, or Firm* — W. Edward Johansen (57) ABSTRACT

An HTML web browser based imaging system which supports acquisition of 2D x-ray radiographs and which includes either a 2D x-ray imaging device or a 2D color imaging device and a client device located in a dental office. Software operating upon the client device and a cloud server with dental imaging software installed and means to receive and store images or image data. The client device and the cloud server are connected either directly or indirectly via either an internet connection or a VPN connection. The client device has capability of the HTML web browser so that it does not require either an add-on extension or plug-in in order to control acquisition of images from a dental x-ray sensor. The software communicates with the dental x-ray sensor and receives image or image data from the dental x-ray sensor. The software receives direction to initiate acquisition and/or to receive image or image data via communication from the application server and/or from the HTML web browser.

10 Claims, 6 Drawing Sheets

(56) References Cited

U.S. PATENT DOCUMENTS

| | | | |
|---|---|---|---|
| 2013/0226993 A1* | 8/2013 | Dorey | H04L 67/10 709/203 |
| 2013/0308839 A1* | 11/2013 | Taylor | G06F 19/321 382/128 |
| 2014/0126715 A1* | 5/2014 | Lum | H04M 3/5133 379/265.09 |
| 2014/0198901 A1* | 7/2014 | Christoff | A61B 6/145 378/98 |
| 2015/0134735 A1* | 5/2015 | Momchilov | G06F 3/14 709/203 |
| 2015/0227638 A1* | 8/2015 | Crucs | G06F 17/30893 715/760 |

\* cited by examiner

Fig. 6

CLOUD BASED 2D DENTAL IMAGING SYSTEM WITH HTML WEB BROWSER ACQUISITION

BACKGROUND OF THE INVENTION

Field of the Invention

This invention relates generally to dental imaging systems and more particularly to intraoral and extraoral 2D imaging systems used to acquire 2D radiographic or color dental images when used in a web (cloud) environment with an HTML web browser and without requiring a plug-in be added to the browser in order to control acquisition of said dental imaging devices.

Description of the Prior Art

Intraoral x-rays and extraoral x-rays have been used in dentistry to image teeth, jaw and facial features for many years. In general this process involves generating x-rays from either an intraoral x-ray source or an extraoral x-ray source, directing the x-ray source at the patient's oral cavity and placing an image receptor device such as either a film or an electronic sensor to receive x-rays from either the intraoral x-ray source or the extraoral x-ray source. X-rays are attenuated by different amounts depending on the dental structure being x-rayed and whether it is bone or tissue. The resulting x-ray photons that pass through either the bone or tissue then form an image on the image receptor either the film or the electronic sensor. This image is then either developed (in the case of the film) or processed and displayed on a computer monitor in the case of the electronic sensor. Intraoral sensors are deployed to users by connecting the sensor to a PC or MAC which is located in the dental office. Local client/server software is installed on the client's PC. Images are saved to a server located in the dental practice. Likewise extraoral sensors (panoramic/cephalometric) are also located in the dental office. Local client/server software is also installed on the client's PC. Images are acquired by the local client server software and saved to a local server on a local area network. As software development methods and principles combined with new topology and deployment models have advanced, systems such as web (cloud) based imaging systems are desirable by users and vendors of dental imaging systems. These types of software applications generally employ software that is installed and deployed via a centrally located application server and maintained by professional IT personnel. The server is connected by a VPN/Internet connection to a remote location/office where clients who are running computers with a HTML web browser can display results of the imaging software located on the application server. Minimal if any add-on or proprietary software is actually installed on the client in a cloud environment which greatly reduces the customer requirement of having to install and maintain software or software upgrades. Additionally, because all images are maintained in cloud storage on the web, the images are automatically backed up and disaster recovery available. And finally, images in the cloud are available for viewing from any location which has any device that has a web browser unlike traditional client/server systems where the images are only readily available inside a local location/office and only when running proprietary locally installed client/server imaging software. Because all intraoral and extraoral x-ray imaging devices require drivers and/or some amount of proprietary software to operate, this limits the ability of the intraoral or extraoral 2D dental x-ray imaging devices to be able to communicate directly with an HTML web browser in the dental office environment for the purposes of acquisition of x-ray images or color images from a color intraoral camera or extraoral camera. In order to be able for HTML web browsers to acquire images or image data from a dental intraoral or extraoral sensor, extensions or plug-ins (add on software) currently must be added to the web browser, which then allows communication with a dental imaging devices proprietary driver and/or application programming interface. These extensions (plug-in or controls) for the browsers are HTML web browser brand specific, for example Google Chrome browser cannot use the same plug-in that would be required for Microsoft Internet Explorer or for Apple Safari browser even when communicating with the same acquisition device. In addition, some browsers can run on different operating systems (Windows, Mac and IOS) and this most times requires the controls to be modified for each operating system as well. The above complexities make real Cloud/Web based imaging not practical or adopted well for 2D dental intraoral and extraoral imaging device users whom desire to acquire and display images via a standard HTML web browser without having to install traditional client server imaging software and/or without having to install, configure and maintain plug-ins for all browsers on all client devices that are desired to support acquisition from a dental imaging device. Indeed, today there exists only one publicly deployed dental cloud imaging application that supports acquisition to the cloud directly from an HTML web browser (Curve Dental/Curve Image) and it operates currently only upon one browser, on select operating systems, and with limited imaging sensor support because of the issues cited above when using a plug-in to control acquisition from a browser. It would be beneficial to allow a dental office to use any HTML web browser, on any operating system, and allow access to locally connected 2D dental imaging devices without adding any specific control, plug-in or add-on to the web browser for the purpose to controlling or directing acquisition from these devices and accomplish the setup and installation of this capability automatically or semi-automatically.

Figure 1:
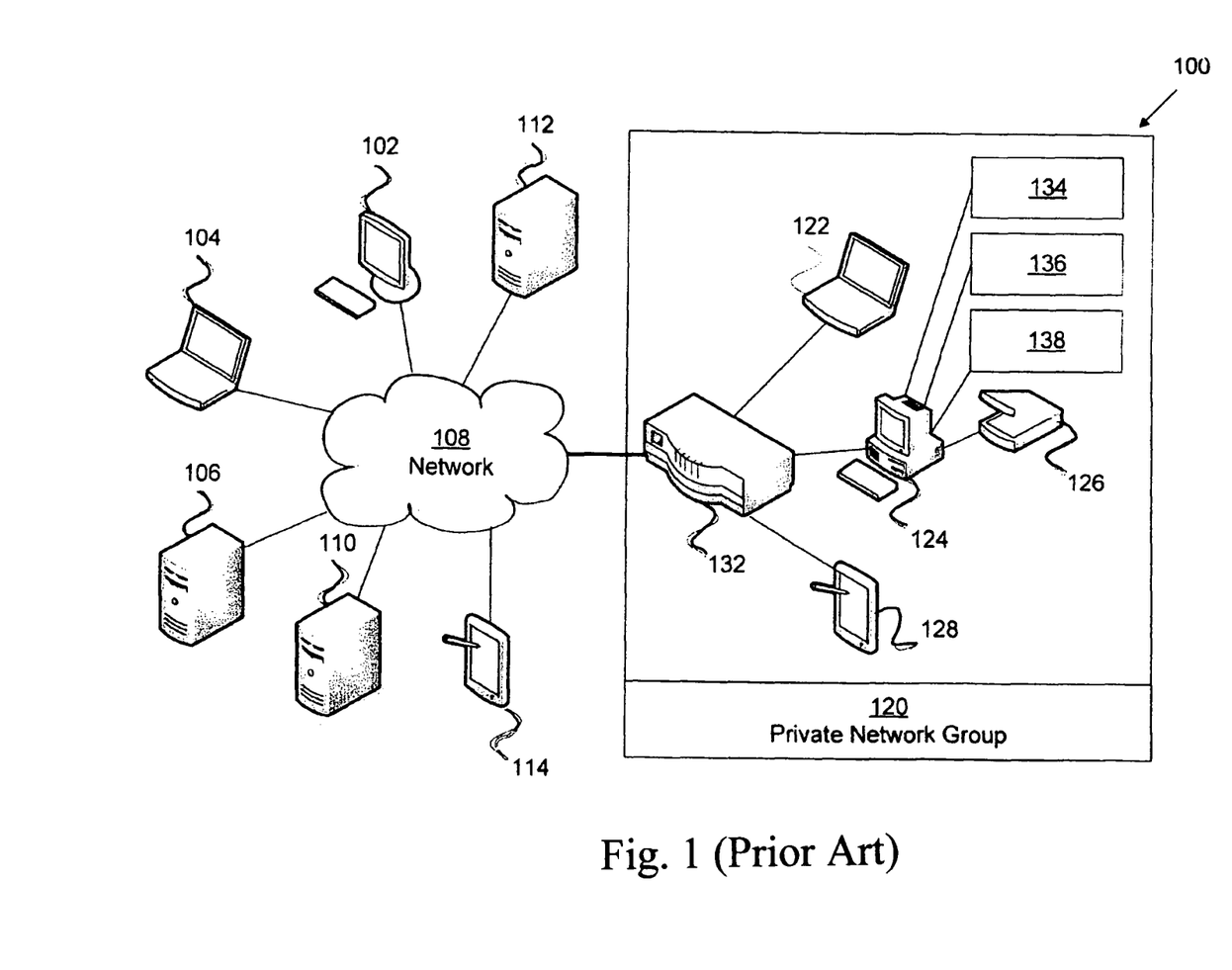
FIG. 1 is a conceptual diagram of a networking system according to U.S. Patent Publication No. 2013/0226993.

U.S. Patent Publication No. 2013/0226993 teaches a media acquisition engine which includes an interface engine that receives a selection from a plug-in coupled to a media client engine where a client associated with the media client engine identified as subscribing to a cloud application imaging service. The media acquisition engine also includes a media control engine that directs, in accordance with the selection, a physical device to image a physical object and produce a media item based on the image of the physical object, the physical device being coupled to a cloud client. The media acquisition engine also includes a media reception engine that receives the media item from the physical device and a translation engine that encodes the media item into a data structure compatible with the cloud application imaging service. The interface engine is configured to transfer the media item to the plug-in. Digital imaging has notable advantages over traditional imaging, which processes an image of a physical object onto a physical medium. Digital imaging help users such as health professionals avoid the costs of expensive processing equipment, physical paper, physical radiographs and physical film. Techniques such as digital radiography expose patients to lower doses of radiation than traditional radiography and are often safer than their traditional counterparts are. Moreover digital images are easy to store on storage such as a computer's hard drive or a flash memory card, are easy transferable, and are more portable than traditional physical images. Further, many digital imaging devices use sophisticated image manipulation techniques and filters that accurately image physical objects. A health professional's information infrastructures and the business processes can therefore potentially benefit from digital imaging techniques. Though digital imaging has many advantages over physical imaging, digital imaging technologies are far from ubiquitous in health offices as existing digital imaging technologies present their own costs. To use existing digital imaging technologies, a user such as a health professional has to purchase separate computer terminals and software licenses for each treatment room. As existing technologies install a full digital imaging package on each computer terminal, these technologies are often expensive and present users with more options than they are willing to pay for. Additionally, existing digital imaging technologies require users to purchase a complete network infrastructure to support separate medical imaging terminals. Users often face the prospects of ensuring software installed at separate terminals maintains patient confidentiality, accurately stores and backs up data, accurately upgrades, and correctly performs maintenance tasks. As such, existing digital imaging technologies are not readily compatible with the objectives of end-users, such as health professionals. Referring to FIG. 1 a networking system 100 for providing one or more application imaging services includes by way a desktop computer 102, a laptop computer 104, a server 106, a network 108, a server 110, a server 112, a tablet device 114, and a private network group 120. The desktop computer 102, the laptop computer 104, the server 106, the server 110, the server 112, and the tablet device 114 are shown directly connected to the network 108, but can be grouped in a manner similar to the private network group 120 without departing from the scope and substance of the inventive concepts disclosed herein. The desktop computer 102 can include a computer having a separate keyboard, monitor, and processing unit. The desktop computer 102 can integrate one or more of the keyboard, the monitor, and the processing unit into a common physical module. The laptop computer 104 can include a portable computer. The laptop 104 can integrate the keyboard, monitor, and processing unit into one physical module. The laptop 104 can also have a battery so that the laptop 104 allows portable data processing and portable access to the network 108. The tablet 114 can include a portable device with a touch screen, a monitor, and a processing unit all integrated into one physical module. Any or all of the computer 102, the laptop 104, and the tablet device 118 can include a computer system. A computer system will usually include a processor, memory, non-volatile storage, and an interface. Peripheral devices can also form a part of the computer system. A typical computer system will include at least a processor, memory, and a bus coupling the memory to the processor. The processor can include a general-purpose central processing unit (CPU), such as a microprocessor, or a special-purpose processor, such as a microcontroller. The memory can include random access memory (RAM), such as dynamic RAM (DRAM) and static RAM (SRAM). The memory can be local, remote or distributed. The term "computer-readable storage medium" includes physical media, such as memory. The bus of the computer system can couple the processor to non-volatile storage. The non-volatile storage is often a magnetic floppy or hard disk, a magnetic-optical disk, an optical disk, a read-only memory (ROM), such as a CD-ROM, EPROM, or EEPROM, a magnetic or optical card, or another form of storage for large amounts of data. A direct memory access process often writes some of this data into memory during execution of software on the computer system. The non-volatile storage can be local, remote or distributed. The non-volatile storage is optional because systems need only have all applicable data available in memory. Software is typically stored in the non-volatile storage. Indeed, for large programs, it may not even be possible to store the entire program in memory. Nevertheless, for software to run, if necessary, it is moved to a computer-readable location appropriate for processing, and for illustrative purposes, this paper refers to that location as the memory. Even when software is moved to the memory for execution, the processor will typically make use of hardware registers to store values associated with the software, and local cache that, ideally, serves to speed up execution. As used herein, a software program is assumed to be stored at any known or convenient location (from non-volatile storage to hardware registers) when the software program is referred to as "implemented in a computer-readable storage medium." A processor is "configured to execute a program" when at least one value associated with the program is stored in a register readable by the processor. The bus can also couple the processor to one or more interfaces. The interface can include one or more of a modem or network interface. A modem or network interface can be part of the computer system. The interface can include an analog modem, isdn modem, cable modem, token ring interface, satellite transmission interface (e.g. "direct PC") or other interfaces for coupling a computer system to other computer systems. The interface can include one or more input and/or output (I/O) devices. The I/O devices can include, by way of example but not limitation, a keyboard, a mouse or other pointing device, disk drives, printers, a scanner, and other I/O devices, including a display device. The display device can include, by way of example but not limitation, a cathode ray tube (CRT), liquid crystal display (LCD), or some other applicable known or convenient display device. Operating system software that includes a file management system, such as a disk operating system, can control the computer system. The operating system software with associated file management system software is the family of operating systems known as Windows from Microsoft Corporation and their associated file management systems. Another example of operating system software with its associated file management system software is the Linux operating system and its associated file management system. The file management system is typically stored in the non-volatile storage and causes the processor to execute the various acts required by the operating system to input and output data and to store data in the memory, including storing files on the non-volatile storage. Some portions of the detailed description refer to algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like. It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices. The algorithms and displays presented herein do not inherently relate to any particular computer or other apparatus. An office can employ one or more of the first physical device 134, the second physical device 136, and the third physical device 138 alone or in combination. Moreover, each of the first physical device 134, the second physical device 136 and the third physical device 138 can reside in a general-purpose computer, such as the desktop computer 124, the tablet device 128, the laptop computer 122, and/or a mobile phone. The networking system 100 can facilitate delivery of a cloud application imaging service. A cloud application imaging service is a service that allows an entity associated with a physical device (such as one of the physical devices 134, 136, and 138) to use a cloud-computing application that is executed on a client computer (such as the desktop computer 124) to direct the physical device to image a physical object. Cloud-based computing, or cloud computing, is a computing architecture in which a client can execute the full capabilities of an application in a container (such as a web browser). Though the application executes on the client, portions of the application can be distributed at various locations across the network. For instance, portions of the cloud application imaging service that are facilitated by the networking system 100 can reside on one or more of the desktop computer 102, the laptop computer 104, the server 106, the server 110, the server 112, the tablet device 114, and/or other locations "in the cloud" of the networking system 100. The application can appear as a single point of access for an end-user using a client device such as the desktop computer 124. The cloud application imaging service can implement cloud client functionalities onto the desktop computer 124. A cloud client incorporates hardware and/or software that allow a cloud application to run in a container such as a web browser. Allowing the desktop computer 124 to function as a cloud client requires the presence of a container in which the cloud application imaging service can execute on the desktop computer 124. The cloud application imaging service can facilitate communication over a cloud application layer between the client engines on the desktop computer 124 and the one or more server engines on the desktop computer 102, the laptop computer 104, the server 106, the server 110, the server 112, the tablet device 114, and/or other locations "in the cloud" of the networking system 100. The cloud application layer or "Software as a Service" (SaaS) facilitates the transfer over the Internet of software as a service that a container, such as a web browser, can access. Thus, as discussed above, the desktop computer 124 need not install the cloud application imaging service even though the cloud application imaging service executes on the desktop computer 124. The cloud application imaging service can also deliver to the desktop computer 124 one or more Cloud Platform as a Service (PaaS) platforms that provide computing platforms, solution stacks, and other similar hardware and software platforms. Moreover, the cloud application imaging service can deliver cloud infrastructure services, such as Infrastructure as a Service (IaaS) that can virtualize and/or emulate various platforms, provide storage, and provide networking capabilities. Accordingly, the cloud application imaging service, consistent with cloud-computing services in general, allows users of the desktop computer 124 to subscribe to specific resources that are desirable for imaging and other tasks related to the physical devices 134, 136, and 138. Providers of the cloud application imaging service can bill end-users on a utility computing basis and can bill for use of resources. In the health context providers of the cloud application imaging service can bill for items such as the number of images an office wishes to process, specific image filters that an office wishes to use, and other use-related factors.

Figure 2:
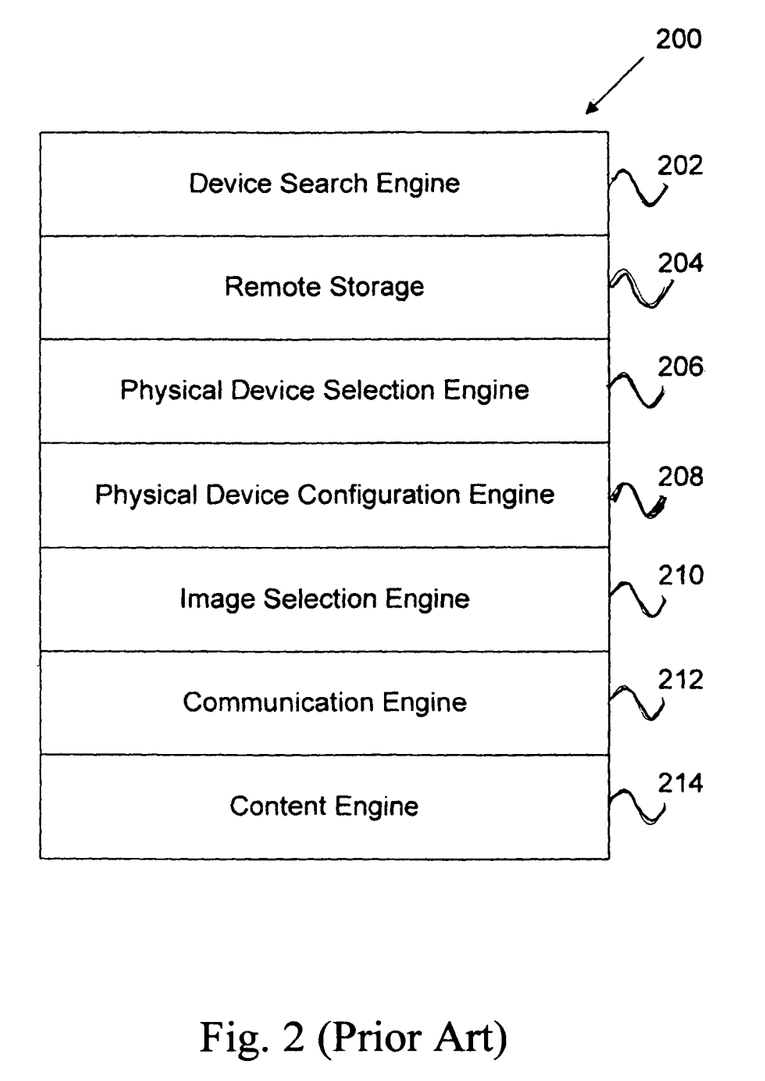
FIG. 2 is a conceptual diagram of a cloud-based server engine according to U.S. Patent Publication No. 2013/0226993.
Figure 3:
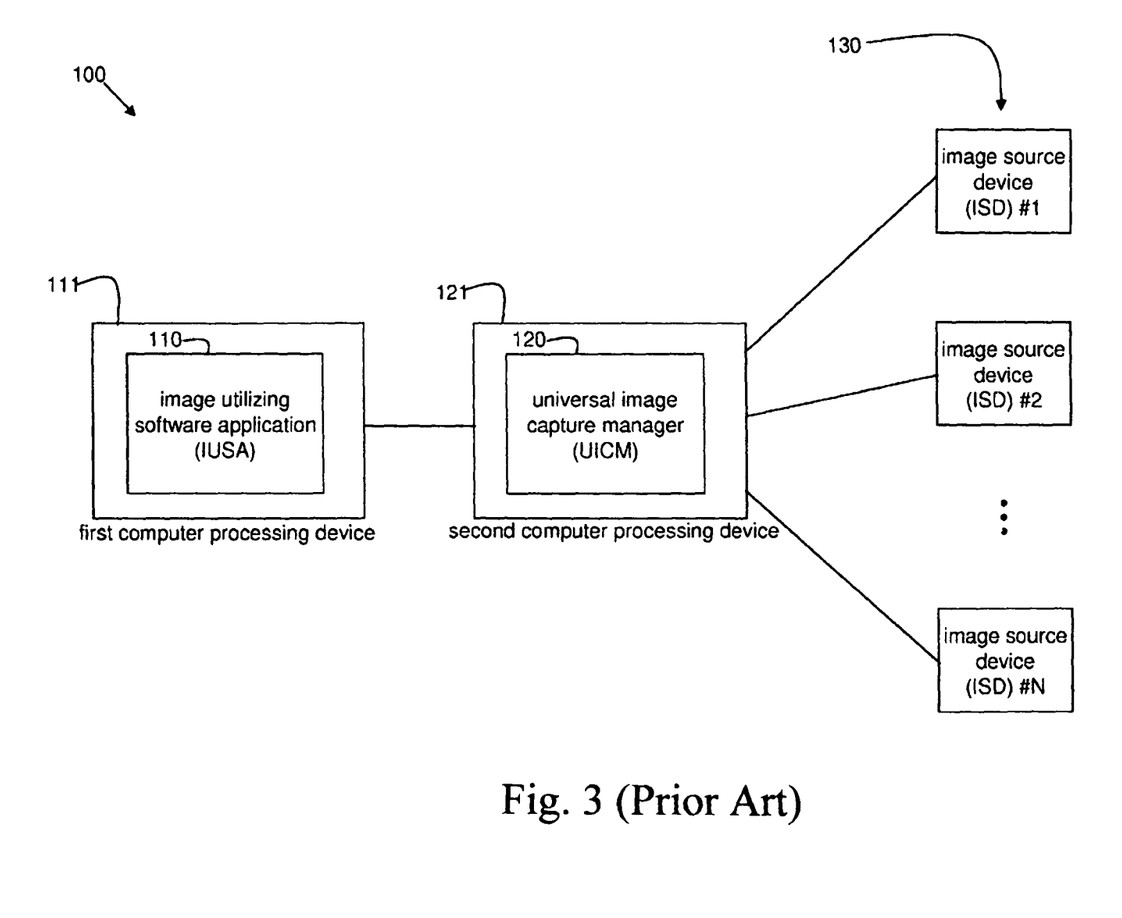
FIG. 3 is a block diagram of a system for acquiring image data from multiple sources according to U.S. Patent Publication No. 2011/0304740.

Referring to FIG. 2 a cloud-based server engine 200 includes a device search engine 202 that searches the physical devices connected to a client computer. The cloud-based server engine 200 also includes remote storage 204 that includes one or more data-stores and/or memory units. The remote storage 204 can include storage on Apache-based servers that are available on a cloud platform such as the EC2 cloud platform made available by Amazon. The cloud-based server engine 200 includes a physical device selection engine 206 that selects a specific physical device connected to a client. The cloud-based server engine 200 can include a physical device configuration engine 208 that configures image parameters and/or attributes of the specific physical device. An image selection engine 210 inside the cloud-based server engine 200 can allow the selection of a specific image from the physical device. A communication engine 212 inside the cloud-based server engine 200 allow the transfer of selection data, parameter data, device data, image data, and other data over a network such as the network 108. The cloud-based server engine 200 also includes a content engine 214 that makes images available to client devices associated with a cloud application imaging service. Processors can control any or all of the components of the cloud-based server engine 200 and these components can interface with data-stores. Any or all of the cloud-based server engines 200 can reside on a computing device such as the desktop computer 102, the laptop 104, the tablet device 114, the server 106, the server 110, and/or server 112. Portions of the cloud-based server engine 200 can also be distributed across multiple electronic devices, including multiple servers and computers.

U.S. Patent Publication No. 2011/0304740 teaches a universal image capture manager (UICM) which facilitates the acquisition of image data from a plurality of image source devices (ISDs) to an image utilizing software application (IUSA). The UICM is implemented on a computer processing device and includes a first software communication interface configured to facilitate data communication between the UICM and an IUSA. The UICM also includes a translator/mapper (T/M) software component being in operative communication with the first software communication interface and being configured to translate and map an image request from an IUSA to at least one device driver (DD) software component of a plurality of DD software components. The UICM further includes a plurality of DD software components being in operative communication with the T/M software component. Each of the DD software components is configured to facilitate data communication with at least one ISD. Many times it is desirable to bring images into a user software application. This is often done in the context of a medical office environment or a hospital environment. Images may be captured by image source devices such as either a digital camera device or an X-ray imaging device and are brought into a user software application such as either an imaging software application or a practice management software application running on either a personal computer or a workstation. Each image source device may require a different interface and image data format for acquiring image data from that image source device. The various interfaces may be TWAIN-compatible or not, may be in the form of an application program interface (API), a data link library (DLL), or some other type of interface. The various image data may be raw image data, DICOM image data, 16-bit or 32-bit or 64-bit image data, or some other type of image data. The process of acquiring an image into a user software application can be difficult and cumbersome. In order to acquire and place an image in a user software application a user may have to first leave the software application, open a hardware driver, set the device options, acquire the image, save the image to a local storage area, close the hardware driver, return to the software application, locate the saved image, and read the image file from the local storage area. Hardware and software developers have developed proprietary interfaces to help solve this problem. Having a large number of proprietary interfaces has resulted in software developers having to write a driver for each different device to be supported. This has resulted in hardware device manufacturers having to write a different driver for each software application. General interoperability between user software applications and image source devices has been almost non-existent. Further limitations and disadvantages of conventional, traditional, and proposed approaches will become apparent to one of skill in the art through comparison of such systems and methods with the present invention as set forth in the remainder of the present application with reference to the drawings. The system 100 acquires image data from multiple sources and includes an image utilizing software application (IUSA) 110 implemented on a first computer processing device 111, a universal image capture manager (UICM) 120 implemented on a second computer processing device 121, and a plurality of image source devices (ISDs) 130 (e.g., ISD #1 to ISD # N, where N represents a positive integer). The IUSA 110 may be a client software application such as an imaging software application or a practice management application as may be used, for example, in a physician's office, a dentist's office, or a hospital environment. The IUSA 110 is implemented on the first computer processing device 111, such as a personal computer (PC) or a work station computer. A plurality of ISDs 130 is hardware-based devices that are capable of capturing images in the form of image data (e.g., digital image data). Examples of such ISDs include a visible light intraoral camera, an intraoral X-ray sensor, a panoramic (pan) X-ray machine, a cephalometric X-ray machine, a scanner for scanning photo-sensitive imaging plates, and a digital endoscope. There exist many types of ISDs using many different types of interfaces and protocols to export the image data from the ISDs. The universal image capture manager (UICM) 120 is a software application or a software module. The second computer processing device 121, having the UICM 120, operatively interfaces between the first computer processing device 111, having the IUSA 110, and the plurality of ISDs 130, and acts as an intermediary between the IUSA 110 and the plurality of ISDs 130. The UICM 120 is a software module implemented on the second computer processing device 121 such as a personal computer (PC), a workstation computer, a server computer or a dedicated processing device designed specifically for UICM operation. The UICM 120 is configured to communicate in a single pre-defined manner with the IUSA 110 to receive image request messages from the IUSA 110 and to return image data to the IUSA 110. The UICM 120 is configured to acquire image data from the multiple image source devices (ISDs) 130. As a result, the IUSA 110 does not have to be concerned with being able to directly acquire image data from multiple different image data sources itself. Instead, the UICM 120 takes on the burden of communicating with the various ISDs 130 and their various communication interfaces and protocols.

U.S. Patent Publication No. 2011/0153351 teaches a system which acquires, hosts and distributes medical images for healthcare professionals. The system includes a database for storing private health information split from a medical imaging record. The system also includes a repository for storing at least one anonymized image split from the medical record. The anonymized images are parsed into a schema upon request with the schema provided in response to the request. The schema can define a structure mapping the anonymized images into a study. The personal information can be joined with the anonymized images to form medical imaging records into the study according to the structure. One or more participant devices in communication with the medical information network can provide collaborative features having application level capabilities that access, process, analyze or augment the personal information from the database and the non-personal information from the repository split from the medical imaging records. The Digital Imaging and Communications in Medicine (DICOM) standard was created by the National Electrical Manufacturers Association (NEMA) for improving distribution and access of medical images, such as CT scans, MRI and x-rays. DICOM arose in an attempt to standardize the image format of different machine vendors (i.e., GE, Hitachi, Philips) to promote compatibility such that machines provided by competing vendors could transmit and receive information between them. DICOM defines a network communication protocol as well as a data format for images. Each image can exist independently as a separate data structure, typically in the form of a textual header followed by a binary segment containing the actual image. This data structure can be commonly persisted as a file on a file system. An image study can be a collection of DICOM images with the same study unique identifier (UID). The study UID can be stored as metadata in the textual header of each DICOM image. The DICOM communication protocol does not comprehend collections of DICOM images into an image study it can only comprehend individual DICOM images. An image study is an abstraction that can be a collection of DICOM images with the same study UID which is beyond the scope of the DICOM communication protocol. Digital medical images are not routinely transported outside of a secure intranet environment over the Internet for two principal reasons. First, medical images are, in most cases, too large to easily email. Second, and more importantly, under the Health Insurance Portability and Accountability Act of 1996 ("HIPAA"), measures need to be taken to provide enhanced security and guarantee privacy of a patient's health information. These requirements cannot be satisfied through routine email or conventional network connections. As a result, if a medical record or imaging study is to be sent from either an imaging center or a hospital to a referring physician's office, a physical film or compact disc (CD) can be printed and hand delivered. Often this is expensive, inaccurate, inefficient and slow. There does not exist today a simple electronic means of moving imaging studies or other medical or similar records among unaffiliated sites. In light of the present methods available for moving medical records, images and other personal information, a need exists for a system and method for providing a secure system for accessing and moving those records among authorized parties. To transmit one or more DICOM images between DICOM devices, a network level DICOM connection can be created between two devices through a TCP/IP communication channel. Once a connection is established, at the discretion of the sender, one or more DICOM images can be transmitted from the sender to the receiver. A sender can choose to send a single DICOM image per DICOM association, a group of images containing the same study UID per DICOM association, or a group of images containing a variety of study UIDs per DICOM association. The receiving DICOM device typically has no protocol level mechanism for determining when it has received all of the DICOM images for a given DICOM study. Convention in the DICOM development community is for a receiving DICOM device to introspect the DICOM header of individual images as they are being received, identify the study UID, and then aggregate the individual images into image studies in a database or on a file system. While this technique is effective to a degree, there is no way for a receiving DICOM device to know when it has received the last image for a given image study. Because of this, it is difficult to determine when to make a study available for a downstream DICOM device or application. A common mitigating technique is to introduce artificial latency, or timers, on a study UID by study UID basis. A timer for a given study UID should expire before making a group of images available to a downstream DICOM device. This industry standard approach attempts to impose a study-oriented communication protocol on top of the inherently image-oriented DICOM protocol. This fundamental mismatch between an image-oriented network protocol and a study-oriented application metaphor creates significant downstream liabilities for clinical radiological workflows. Through artificial latencies, described above, each DICOM device in a clinical workflow can wait a defined amount of time before making studies available to an end user or to a downstream DICOM device. This technique is by definition non-deterministic and non-event driven. A serial sequence of DICOM devices can create a chain of latencies that materially delay the clinical workflow. If additional image content is received after the application defined latency period, then the study can be updated in the downstream devices and user applications, which in turn raises both mechanism and policy issues for clinical DICOM workflow. If a study update is simply adding new images to an existing study, then an additive policy can be implemented by downstream devices and applications. If a study update is modifying data in an existing study, perhaps textual data in the DICOM header that was incorrectly entered by a technician, now there is a possibility that previously processed DICOM data was in error and can be corrected so that any downstream device needs to update the errant DICOM files with the corrected ones. If a study update is attempting to remove previously submitted images, downstream devices and applications need to delete the appropriate DICOM files. Under the current DICOM protocol no mechanism is provided for deleting or correcting errant images, so each device and application addresses this problem based on their own internally derived mechanism and policy. DICOM is a store and forward protocol that is deterministic image by image, but nondeterministic image study by image study. This creates a non-deterministic, study-oriented data flow. DICOM dataflow is the foundation of radiological clinical workflows. Non-deterministic DICOM data-flows introduce non-determinism into the clinical workflow. Getting the right images to the right person at the right time becomes problematic and inefficient. The awkward nature of the study-oriented store and forward of DICOM data lends itself to silo-ed and overlapping repositories of DICOM images inside the four walls of an institution. This creates significant storage inefficiencies and infrastructure carrying costs. It also lends itself to fragmented repositories where there is no single repository that holds all images for a given facility. This introduces challenges when treating return patients where access to prior imaging studies is fundamental to the clinical process. Silo-ed images, accessible through an artificial application level image study metaphor, create an opaque domain model for images in an image study with no visibility into the relative importance of images. The clinical reality is that some images are more valuable than others. The more important images are frequently tagged by radiologists as "key" images and annotated or post-processed to enhance the imaging data within the image. Key images and the images immediately adjacent to key images are often the high value content within an image study. Downstream referring physicians typically do not want to view an entire image study they want to view the small subset of high value images. But study oriented processing is opaque in the fact that there is no ability to distinguish the relevancy of images within the study. Optimized radiological workflow demands appropriate mechanisms for data relevancy and study oriented processing inhibits these mechanisms. In current systems, providing collaborative features to access medical images over the web creates numerous challenges. Standard protocols do not exist for those systems described in the previously filed applications. It would be desirable to provide a medical information network with collaborative medical imaging web applications that overcome the above described issues as well as provide other related advantages.

U.S. Pat. No. 7,457,656 teaches a medical image management system which allows any conventional Internet browser to function as a medical workstation and which may be used to convert medical images from a plurality of image formats to browser compatible format. The system manipulates digital medical images in such a way that multiple imaging modalities from multiple different vendors can be assembled into a database of Internet standard web pages without loss of diagnostic information. Medical imaging is important and widespread in the diagnosis of disease. In certain situations, however, the particular manner in which the images are made available to physicians and their patients introduces obstacles to timely and accurate diagnoses of disease. These obstacles generally relate to the fact that each manufacturer of a medical imaging system uses different and proprietary formats to store the images in digital form. This means, for example, that images from a scanner manufactured by General Electric Corp. are stored in a different digital format compared to images from a scanner manufactured by Siemens Medical Systems. Images from different imaging modalities, such as ultrasound and magnetic resonance imaging (MRI) are stored in formats different from each other. Although it is typically possible to "export" the images from a proprietary workstation to an industry-standard format such as "Digital Imaging Communications in Medicine" (DICOM), Version 3.0, several limitations remain as discussed subsequently. In practice, viewing of medical images typically requires a different proprietary "workstation" for each manufacturer and for each modality. Currently, when a patient describes symptoms the patient's primary physician often orders an imaging-based test to diagnose or assess disease. Days after the imaging procedure the patient's primary physician receives a written report generated by a specialist physician who has interpreted the images. The specialist physician typically has not performed a clinical history and physical examination of the patient and often is not aware of the patient's other test results. Conversely, the patient's primary physician typically does not view the images directly but rather makes a treatment decision based entirely on written reports generated by one or more specialist physicians. Although this approach does allow for expert interpretation of the images by the specialist physician, several limitations are introduced for the primary physician and for the patient such as: (1) The primary physician does not see the images unless he travels to another department and makes a request; (2) It is often difficult to find the images for viewing because there typically is no formal procedure to accommodate requests to show the images to the primary physician; (3) Until the written report is forwarded to the primary physician's office it is often difficult to determine if the images have been interpreted and the report generated; (4) Each proprietary workstation requires training in how to use the software to view the images; (5) It is often difficult for the primary physician to find a technician who has been trained to view the images on the proprietary workstation; (6) The workstation software is often "upgraded" requiring additional training; (7) The primary physician has to walk to different departments to view images from the same patient but different modalities; (8) Images from the same patient but different modalities cannot be viewed side-by-side, even using proprietary workstations; (9) The primary physician cannot show the patient his images in the physician's office while explaining the diagnosis; and (10) The patient cannot transport his images to another physician's office for a second opinion. It would be desirable to allow digital medical images to be viewed by multiple individuals at multiple geographic locations without loss of diagnostic information. "Teleradiology" allows images from multiple scanners located at distant sites to be transferred to a central location for interpretation and generation of a written report. This model allows expert interpreters at a single location to examine images from multiple distant geographic locations. Tele-radiology does not allow for the examination of the images from any site other than the central location, precluding examination of the images by the primary physician and the patient. Rather the primary physician and the patient see only the written report generated by the interpreters who examined the images at the central location. In addition, this approach is based on specialized "workstations" (which require substantial training to operate) to send the images to the central location and to view the images at the central location. It would be advantageous to allow the primary physician and the patient to view the images at other locations, such as the primary physician's office, at the same time he/she and the patient see the written report and without specialized hardware or software. In principle, medical images could be converted to Internet Web Pages for widespread viewing. Several technical limitations of current Internet standards create a situation where straightforward processing of the image data results in images which transfer across the Internet too slowly, lose diagnostic information or both. One such limitation is the bandwidth of current Internet connections which, because of the large size of medical images, result in transfer times which are unacceptably long. The problem of bandwidth can be addressed by compressing the image data before transfer, but compression typically involves loss of diagnostic information. In addition, due to the size of the images the time required to process image data from an original format to a format which can be viewed by Internet browsers is considerable, meaning that systems designed to create Web Pages "on the fly" introduce a delay of seconds to minutes while the person requesting to view the images waits for the data to be processed. Workstations allow images to be reordered or placed "side-by-side" for viewing, but again, an Internet system would have to create new Web Pages "on the fly" which would introduce further delays. Finally, diagnostic interpretation of medical images requires the images are presented with appropriate brightness and contrast. On proprietary workstations these parameters can be adjusted by the person viewing the images but control of image brightness and contrast are not features of current Internet standards (such as, for example, http or html). It is possible to allow browsers to adjust image brightness and contrast, as well as other parameters, using "Java" programming. "Java" is a computer language developed by Sun Microsystems specifically to allow programs to be downloaded from a server to a client's browser to perform certain tasks. Using the "Java" model the client is no longer simply using the browser to view "static" files downloaded from the server, but rather in addition the client's computer is running a program that was sent from the server. There are several disadvantages to using "Java" to manipulate the image data. First, the user must wait additional time while the "Java" code is downloaded. For medical images, the "Java" code is extensive and download times are long. Second, the user must train to become familiar with the controls defined by the "Java" programmer. Third, the user must wait while the "Java" code processes the image data, which is slow because the image files are large. Fourth, "Java" code is relatively new and often causes browsers to "crash." Finally, due to the "crashing" problem "Java" programmers typically only test their code on certain browsers and computers, such as Microsoft Explorer on a PC, precluding widespread use by owners of other browsers and other computer platforms.

U.S. Pat. No. 5,891,035 teaches an ultrasound system which incorporates an http server for viewing ultrasound images over the Internet. The approach creates Web Pages "on the fly," meaning that the user must wait for the image processing to complete. In addition, even after processing of the image data into a Web Page this approach does not provide for processing the images in such a way that excessive image transfer times due to limited bandwidth are addressed or provide for "brightness/contrast" to be addressed without loss of diagnostic information. In addition this approach is limited to ultrasound images generated by scanners manufactured by a single company, and does not enable viewing images from modalities other than ultrasound. Serial processing of image data "on the fly" combined with extensive user interaction results in a slow, expensive, and unstable system. After a scanner acquires images a user may request single image as a webpage. The image data is downloaded to allow the user to view a single image with the single image. The steps taken result in extensive user interaction which results in the system being slow, expensive and unstable.

U.S. Pat. No. 8,073,712 teaches medical records, clinical observations and medical imagery which are organized and aggregated into a common database thereby enabling the data to be viewed and/or updated by medical-practitioners world-wide. The information may also be viewed and monitored by patients or their relatives for accuracy regardless of their location. The records may be updated by manually controlled or automated instrumentation which measures medical parameters whether located in a doctor's office, in a hospital setting, in the patient's home or worn by the patient. Common access and point-to-point data transmission is via the global grid, or over public access common data networks supporting TCP/IP, most often referred to as the Internet. The same approach can be using insider an organization over an internal network or Intranet. This management of medical/dental patient records is a method for storing and accessing such records through the world-wide-web. Medical records are currently prepared and stored by hand in physical files, by machine and converted to physical form through print outs for storage in physical files, or by machine and stored in digital form. The typical arrangement is to use all of these means in a complex mixture within a medical facility. The normal evolution of digital medical record preparation and storage has been within a particular doctor's practice, clinic or hospital facilities grouping. With the advent of managed care networks, proprietary systems for providing network access to the data have been built, however, no large area, multi-institution, national or international medical repository has yet been built. There are several reasons for the lack of a centralized database. First is the importance of maintaining the privacy of data. It is also difficult to exchange data between proprietary systems which code the same types of data differently. Another problem arises from the fact that different medical establishments store some data in digital exchangeable form and other data in less portable forms (paper and film). There is currently no universal agreement as to which data is stored in what form. Medical establishments also gain a high degree of proprietary ownership of the patient when they retain the patient's medical information, even though they typically exchange data with each other when specifically requested to do so by the patient. The primary efforts to implement a universal standard for medical data exchange have been driven by standards organizations. One example is the Andover Group, a non-profit organization which was originally organized by Hewlett Packard, but has since been joined by several hundred other organizations and companies. Andover Group has not defined standards for interoperation, but rather has endorsed existing standards. These are principally DICOM, an ISO standard for encoding medical image data, IEEE 1073, a networking and protocol standard for collecting and transmitting clinical observation data (such as from EKG or vital signs instruments), and HL7, an encoding method for patient medical records which include billings data and chart data. Another example is the IEEE 1073 standards organization, which is organized to define an IEEE standard for networking and protocols for collecting and transmitting clinical observation data (such as from EKG or vital signs instruments). This group was formed in 1985 when many efforts to define application-specific alternatives to IEEE 802.3, or Ethernet, were prevalent. The 1073 committee took this route in the medical field, citing that normal Ethernet did not deliver predictable data delivery timing (because it uses collision detect multiple access to media allocation), and did not provide proper interconnect for use in the medical field (which included instrument isolation, quick connect, disconnect, and star configuration wiring). The 1073 committee has successfully defined 1073.1, the interconnect technology standard, but has to date failed to complete 1073.2 and up, which define standard protocols and encodings for clinical instrument data streams. Unfortunately, in 1999, Ethernet variations no longer have the cited interconnect limitations cited in 1985, which puts into doubt the value of 1073.1. Ethernet, in the 10 and 100 baser configurations, allows a quick connect/disconnect from star networks emanating from standard hubs (which are interconnects at the phone closet). Wireless Ethernet adapters allow connections to local routers without any connection and by using routers and gateways to connect instrument, room level or unit level sub-networks any degree of desired data delivery latency can be achieved. As it stands, 1073.1 may never gain widespread acceptance. DICOM is an ISO standard which was defined to allow encoding and exchange of X-ray, CAT, and other digital image format data easily. Unfortunately, much medical imagery is still stored primarily on film, which must be physically copied and exchanged. Until the common X-ray machine is fully digital this will remain the case. HL7 is tagged object encoding formatted, defined for medical institutions to exchange medical records between dissimilar central computer systems. HL7 is gaining widespread acceptance as the main way for hospitals to exchange their data without paper files as the intermediary. This acceptance does not yet represent a majority of institutions. As indicated in the next paragraph, HL7 is by no means the only standard being considered. Common Object Request Brokering Application (COBRA) is a method defined and maintained by the Object Management Group (OMG). OMG acts as a clearing house for organizations building object oriented interoperable software/systems applications. OMG organizes standards committees much like the IEEE, ANSI, or ISO, but is centered-around object oriented programming methodology. CORBA is OMG's framework for all of these standards activities. Within the CORBA umbrella is the CORBA-med group. CORBA-med is focused on defining interoperable medical applications and standards which leverage the basic CORBA object oriented messaging and coding approach. CORBA-med has units which are concerned with defining interoperability with HL7 (and actually coding versions of HL7) within CORBA. CORBA-med is also currently defining Clinical Observation and Analysis Systems (COAS) using COBRA methods. CORBA-med is very much a counter point to the Andover Group, IEEE 1073, and HL7. A similar effort at Microsoft to leverage COM, an alternative common object model has begun to address medical data management applications. A method of managing medical information includes the step of receiving at a first computer a plurality of image series resulting from a patient medical imaging procedure. Each image series includes one or more digital medical images in a format that is incompatible with displaying in an Internet web browser thereby providing a pointer associated with the patient medical imaging procedure. In response to user selection of the pointer at a second computer the series provides an Internet web page for display in an Internet web browser on the second computer. The Internet web page forms a user interface for a medical image workstation when displayed in the Internet web browser without requiring software executing outside the Internet web browser on the second computer. The user interface includes a rectangular grid of one or more rows and one or more columns for simultaneously displaying a plurality of navigational images in the user interface of the Internet web page and providing to the user the plurality of navigational images for display in the user interface of the Internet web page. The plurality of navigational images corresponds to different ones of the image series from the patient medical imaging procedure. The plurality of navigational images includes a format that is compatible for displaying in an Internet web browser without requiring software executing outside the Internet web browser on the second computer. The plurality of navigational images is converted to a browser compatible format before being transmitted over the Internet in response to user selection of one of the plurality of navigational images providing to the user the one or more digital medical images of the image series associated with the selected one of the navigational images for display in the user interface of the Internet web page. The one or more digital medical images includes a format that is compatible for displaying in the Internet web browser without requiring software executing outside the Internet web browser on the second computer. The one or more digital medical images provide medical information to the user. The one or more digital medical images are converted to a browser compatible format before being transmitted to the second computer. The medical image workstation enables user navigation among the plurality of navigational images and the one or more digital medical images of the image series to permit medical diagnosis from the one or more digital medical images without requiring software executing outside the Internet web browser. Medical imaging is important and widespread in the diagnosis of disease. In certain situations, however, the particular manner in which the images are made available to physicians and their patients introduces obstacles to timely and accurate diagnoses of disease. These obstacles generally relate to the fact that each manufacturer of a medical imaging system uses different and proprietary formats to store the images in digital form. This means that images from a scanner manufactured by General Electric are stored in a different digital format compared to images from a scanner manufactured by Siemens Medical Systems. Images from different imaging modalities, such as ultrasound and magnetic resonance imaging (MRI), are stored in formats different from each other. Although it is typically possible to "export" the images from a proprietary workstation to an industry-standard format such as "Digital Imaging Communications in Medicine" (DICOM), Version 3.0, several limitations remain as discussed subsequently. In practice, viewing of medical images typically requires a different proprietary "workstation" for each manufacturer and for each modality. Currently, when a patient describes symptoms, the patient's primary physician often orders an imaging-based test to diagnose or assess disease.

U.S. Pat. No. 5,924,074 teaches how text-type patient record data can be created and maintained electronically. This information includes complaints, lab orders, medications, diagnoses, and procedure descriptions. The description is of a specific implementation which appears to map directly on the structure described by documents associated with the definition of HL7, the standard for hospital and medical data record exchange. The key patented innovation is using pen-based portable computer interfaces. If the user prefers a portable user interface, a pen-portable computer would be appropriate, however, normal web-data terminal interfaces are usable as well.

U.S. Pat. No. 6,032,119 teaches a display of individualized patient health status on a HTML display which depicts the human body. This is an interesting display method, but is limited to the specific integration of data required for the display coupled to its representation format. It does not describe archival or data collection specifically. None of these standards efforts have addressed combining all medical data into a common database accessible or updateable from anywhere by anyone with appropriate access rights. Current methods do not teach how all forms of medical data from all sources are read in initially and updated routinely, nor do they explain how all forms of medical data from all sources are viewed and/or updated manually by patients, doctors, or other medical staff.

U.S. Pat. No. 8,166,381 teaches a method of managing medical information. Medical image data is received at a real-time transfer engine at the same time that the patient is being scanned by a medical imaging device. The medical image data is then converted to a browser-compatible image format at a converter engine connected to receive the medical image data from the real-time transfer engine. The converter engine includes a decoder engine for extracting image pixel data from the medical image data and an encoding engine for converting the image pixel data to a browser-compatible format connected to receive the image pixel data. The image pixel data may be converted to a browser compatible format without loss of diagnostic data.

U.S. Patent Publication No. 2013/0208955 teaches a cloud server which receives over a network a request for accessing three-dimensional (3D) medical image data from a first user. The cloud server provides image processing services to a plurality of users using a plurality of image processing tools provided by the cloud server. The cloud server determines user privileges of the users for accessing the 3D medical image data. The user privileges are related to the 3D medical image data. The 3D medical image data was captured by a medical imaging device and stored in storage associated with the cloud server. The availability of the image processing tools is limited to the user to process the 3D medical image data based on the user privileges. A computerized axial tomography scan (commonly known as a CAT scan or a CT scan) is an x-ray procedure, which combines many x-ray images with the aid of a computer to generate cross-sectional views of the internal organs and structures of the body. In each of these views, the body image is seen as an x-ray "slice" of the body. Typically, parallel slices are taken at different levels of the body, i.e., at different axial (z-axis) positions. This recorded image is called a tomogram and "computerized axial tomography" refers to the recorded tomogram "sections" at different axial levels of the body. In a multi-slice CT, a two-dimensional (2D) array of detector elements replaces the linear array of detectors used in conventional CT scanners. The 2D detector array permits the CT scanner to simultaneously obtain tomographic data at different slice locations and greatly increases the speed of CT image acquisition. The multi-slice CT facilitates a wide range of clinical applications including three-dimensional (3D) imaging with a capability for scanning large longitudinal volumes with high z-axis resolution. Magnetic resonance imaging (MRI) is another method of obtaining images of the interior of objects, especially the human body. An MRI is a non-invasive, non-x-ray diagnostic technique employing radio-frequency waves and intense magnetic fields to excite molecules in the object under evaluation. Like a CAT scan, the MRI provides computer-generated image "slices" of the body's internal tissues and organs. As with the CAT scans, the MRI facilitates a wide range of clinical applications including 3D imaging and provides large amounts of data by scanning large volumes with high resolution. Medical image data which are collected with medical imaging devices, such as X-ray devices, MRI devices, Ultrasound devices, Positron Emission Tomography (PET) devices or CT devices in the diagnostic imaging departments of medical institutions, are used for an image interpretation process called "reading" or "diagnostic reading." After an image interpretation report is generated from the medical image data, the image interpretation report, possibly accompanied by representative images or representations of the examination, are sent to the requesting physicians. Today, these image interpretation reports are usually digitized, stored, managed and distributed in plain text in a Radiology Information System (RIS) with accompanying representative images and the original examination stored in a Picture Archiving Communication System (PACS) which is often integrated with the RIS. Typically, prior to the interpretation or reading, medical images may be processed or rendered using a variety of imaging processing or rendering techniques. Recent developments in multi-detector computed tomography (MDCT) scanners and other scanning modalities provide higher spatial and temporal resolutions than the previous-generation scanners. Advanced image processing was first performed using computer workstations. However, there are several limitations to a workstation-based advanced image processing system. The hardware and software involved with these systems are expensive and require complicated and time consuming installations. Because the workstation can only reside in one location, users must physically go to the workstation to use the advanced image processing software and tools. Also, only one person can use the workstation at a time. Some have improved on this system by converting the workstation-based advanced image processing system to a client-server-based system. These systems offer some improvements over the workstation-based systems in that a user can use the client remotely so that the user does not have to be physically located near the server, but can use his/her laptop or computer elsewhere to use the software and tools for advanced image processing. Also, more than one client can be used with a given server at one time so that more than one user can simultaneously and remotely use the software that is installed on one server. The computational power of the software in a client-server-based system is distributed between the server and the client. In a "thin client" system, the majority of the computational capabilities exist at the server. In a "thick client" system more of the computational capabilities and possibly data exist on the client. The hardware software installation and maintenance costs and complexity of a client-server based system are still drawbacks. Also, there can be limitations on the number of simultaneous users that can be accommodated. Hardware and software must still be installed and maintained. Generally the information technology (IT) department of the center which purchased the system must be heavily involved. This can strain resources and complicate the installation and maintenance process.

The inventor hereby incorporates all of the above referenced patents into this specification.

SUMMARY OF THE INVENTION

The present invention relates generally to an HTML web browser based imaging system which supports acquisition of 2D x-ray radiographs and which includes either a 2D x-ray imaging device or a 2D color imaging device located in a dental office and a client device with capability of a HTML web browser also located in the dentist office.

In the first aspect of the present invention the capability of the HTML web browser does not require either an add-on extension or plug-in in order to control acquisition of images from a dental x-ray sensor.

In the second aspect of the present invention the HTML web browser based imaging system includes software operating upon the client device. The software communicates either directly or indirectly with the dental x-ray sensor and receives image or image data from the dental x-ray sensor. The software receives direction to initiate acquisition and/or to receive image or image data via communication from the application server and/or from the HTML web browser of the client device.

In the third aspect of the present invention the HTML web browser based imaging system includes a cloud server with dental imaging software installed and means to receive and store images or image data. The client device with the HTML web browser and the cloud server are connected either directly or indirectly via either an internet connection or a VPN connection.

In the fourth aspect of the present invention the software is either a mini-application or provided by a software service.

In the fifth aspect of the present invention the 2D x-ray imaging device is an intraoral 2D x-ray imaging device and the dental x-ray sensor is a dental intraoral x-ray sensor so that the cloud server receives and stores intraoral images.

In the sixth aspect of the present invention the 2D x-ray imaging device is an extraoral 2D x-ray imaging device and the dental x-ray sensor is a dental extraoral x-ray sensor so that the cloud server receives and stores extraoral images.

In the seventh aspect of the present invention the capability of the HTML web browser does not require either an add-on extension or plug-in in order to control acquisition of images from a camera.

In the eighth aspect of the present invention the HTML web browser based imaging system includes software operating upon the client device. The software communicates directly or indirectly with the camera and receives image or image data from the camera. The software receives direction to initiate acquisition and/or to receive image or image data via communication from the application server and/or from the HTML web browser of the client device.

In the ninth aspect of the present invention the HTML web browser based imaging system includes a cloud server with dental imaging software installed and means to receive and store images or image data. The client device with the HTML web browser and the cloud server are connected directly or indirectly via either an internet connection or a VPN connection.

In the tenth aspect of the present invention the camera is a dental 2D color still camera.

In the eleventh aspect of the present invention the camera is a dental 2D color video camera.

In the twelfth aspect of the present invention the software is a mini-application.

In the thirteenth aspect of the present invention the software is provided by a software service.

In the fourteenth aspect of the present invention the 2D color dental imaging device is an intraoral 2D color dental camera so that the cloud server receives and stores 2D color intraoral images.

In the fifteenth aspect of the present invention the 2D color dental imaging device is an extraoral 2D color dental camera so that the cloud server receives and stores 2D color extraoral images.

Other aspects and many of the attendant advantages will be more readily appreciated as the same becomes better understood by reference to the following detailed description and considered in connection with the accompanying drawing in which like reference symbols designate like parts throughout the figures.

DESCRIPTION OF THE PREFERRED EMBODIMENT

Figure 4:
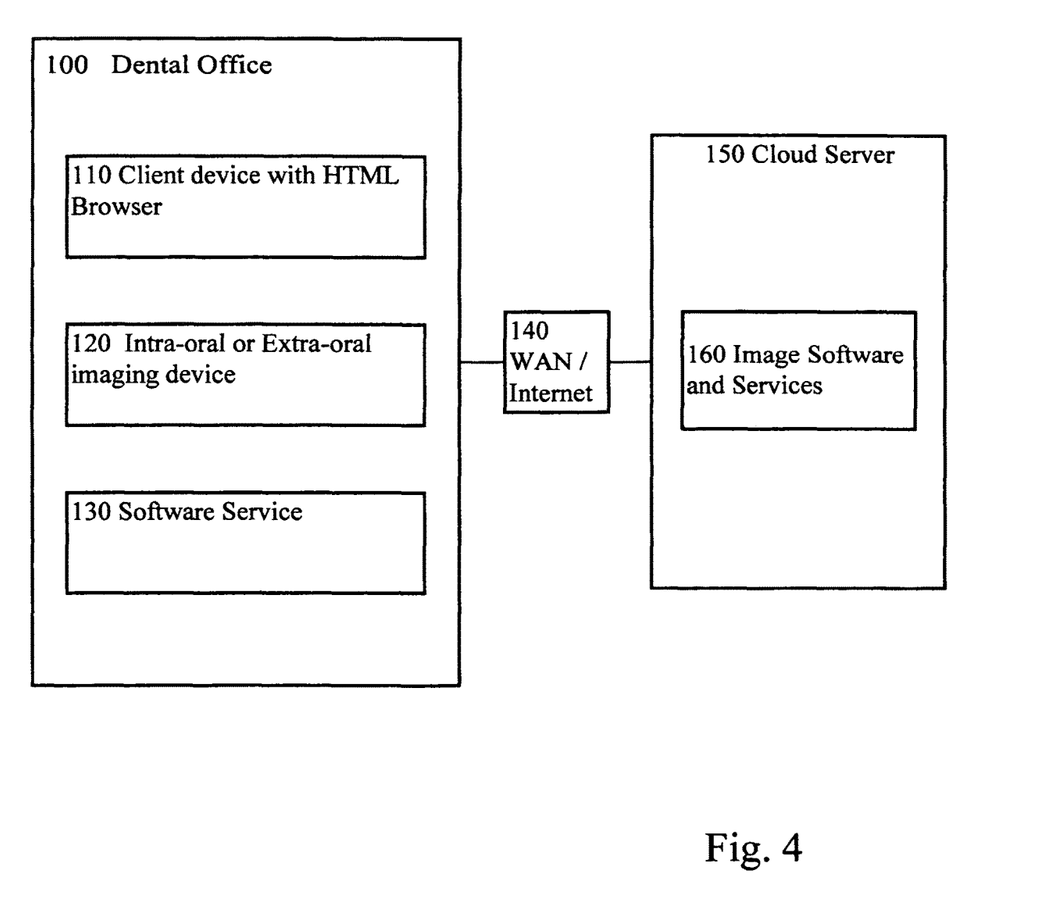
FIG. 4 is a schematic diagram of a dentist office with a wan/internet connection and a cloud server according to the present invention.

Referring to FIG. 4 a dentist office 100 has a wan/internet connection 140 and a cloud server 150. The dentist office 100 includes client device 110, a software service 130 and an intraoral/extraoral imaging device 120. Cloud server 150 includes dental imaging software and services and storage 160. A software service/mini-application that can be added automatically at the direction of the cloud software application from the application server by means of detecting or receiving what operating system is in use upon the client when the client device connects to the cloud server. Any required software for a specific dental imaging device such as device driver or application programming interface software and specifically for the detected operating system is downloaded to the client automatically. This operation only requires obtaining the operating system upon which the client is running and the sensor the user desires to connect to the local client or local network. The client service is then configured automatically for a specific dental imaging device prior to downloading from the application server based upon the automatic detection of the dental imaging device that is connected to the client when the client connected to the cloud application server. If a dental imaging device is not connected to the client, the software may display to the user a list of supported dental imaging devices from which the user can select one for use on this client or can be prompted to connect the device to be used on this client and retry automatic detection. The service that runs on the client device operating system such as Windows, OS X, IOS, Android, or Linux installs any specific sensor driver if required or not previously installed, which was downloaded automatically in the previous step and which does all communication with the physical sensor. The application server communicates and in one embodiment can receive input from the HTML web browser, for example a user clicked a button to "Arm Sensor for Exposure" which then causes the application server to communicate with the local service operating on the client device, and then the local service communicates with the connected sensor and directs the sensor device driver and/or API to arm sensor for exposure. When the sensor is exposed and the image or image data is retrieved by the local service on the client device, the service notifies the application server that a new image is available; which then is uploaded to the cloud server, saved in a database or as a reference in a database, and then notification and display in the client's standard HTML web browser.

Referring to FIG. 4 the dentist office 100 has a local client device 110 which has ability to operate a standard HTML web browser which has not had a plug-in or extension added to support acquisition from dental imaging device 120. The local client device 110 also operates a local software service 130. The application server 150 includes image software and services and storage 160 and has means to automatically detect what intraoral or extraoral imaging device 120 is currently connected to client device 110 via communicating across internet/wan connection 140. When a user connects a dental imaging device 120 to client device 110, service 130 automatically prepares the sensor to take an image. The user can then expose the dental imaging device 120 and the image or image data is automatically sent to cloud server 150 for permanent storage by cloud imaging software and services 160. Cloud software 160 then can notify a client device or devices; if any are currently connected, that an image is available. If client device 110 is not connected to cloud software 160; the cloud software 160 can notify of image availability when a client device or specific user does connect. This workflow using the invention allows acquiring images or image data quickly and automatically without requiring any user input, device selection or modality selection.

Figure 5:
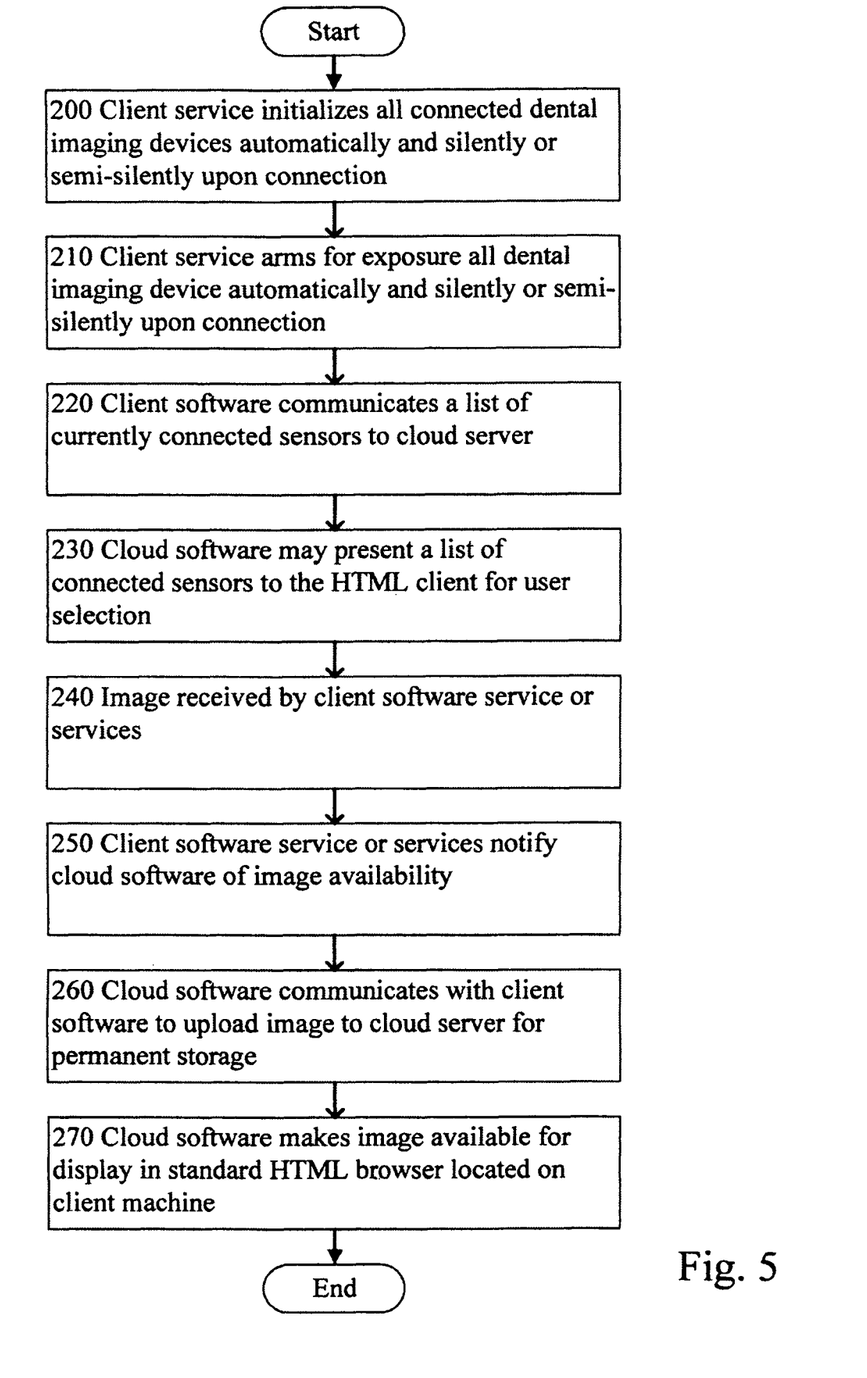
FIG. 5 is a flowchart of the first preferred embodiment of the present invention.

Referring to FIG. 5 a flowchart of workflow shows the client service initializing all connected dental imaging devices automatically in step 200. In step 210, all initialized devices are automatically armed for exposure. In step 220, the client software may communicate a list of currently connected sensors. In step 230, the cloud software may present a list of connected devices to the HTML client for user selection. In step 240, whether or not a client selected an imaging device, the service receives an image or image data from the dental imaging device. The client software communicates with the cloud software in step 250 and notification of image availability is received. In step 260, the cloud software communicates with the client software to upload the image to the cloud server for storage. And finally in step 270, the cloud software makes the image or image data available for display in standard HTML web browser located on client machine.

Referring again to FIG. 4 a block diagram contains local client device 110 which has the ability to operate a standard HTML web browser and which has not had a plug in or extension added to support acquisition from dental imaging device 120. Client device 110 issues an "Arm for Exposure" command to the cloud software 160 on cloud server 150. The cloud software issues an arm for exposure command to the client service or services 130 which are operating on client device 110. The cloud service checks for a sensor and initializes the sensor, if present, in order to arm the sensor for exposure. The client service 130 responds with error or status information to cloud server software 160. The cloud software communicates this information to the HTML web browser on client device 110. The client service 130 notifies the cloud server software 160 when and if an image or image data is available from the service 130. The software service 130 uploads the image or image data to the cloud server 150 for permanent storage. The cloud software 160 communicates the image for display in a standard HTML browser on the client device 110. This workflow using the invention allows acquiring images or image data from a pre-defined imaging device, or user selected imaging device; or automatically selected device via detecting the currently connected dental imaging device 120; and simultaneously allows pre-exposure commands to be communicated via client device 110 to cloud software 160 and software service 130 to dental imaging device 120.

Figure 6:
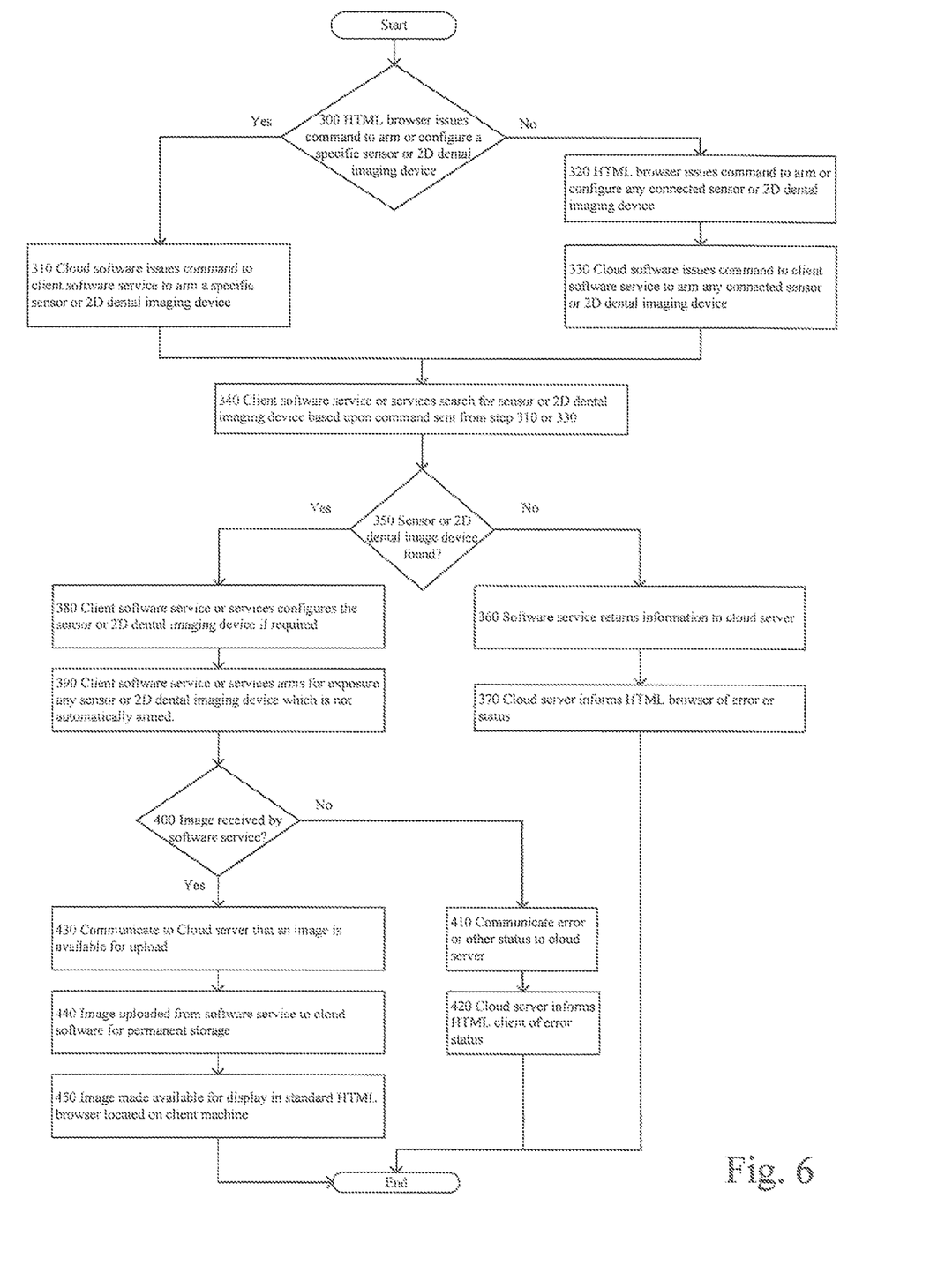
FIG. 6 is a flowchart of the second preferred embodiment of the present invention.

Referring to FIG. 6 a flowchart of workflow in step 300 the HTML web browser may receive a command to arm or configure a specific sensor via user input. If the browser software determines the user input was for a specific sensor or 2D dental imaging device then it goes to step 310 and the cloud software issues a command to the client service to arm a specific sensor. If the software determines that the user input was to arm any connected sensor rather than a specific sensor or 2D imaging device then in step 320 the html web browser issues a command to cloud server to arm any connected sensor. In Step 340 the client software service or services search for a sensor or 2D imaging device based upon input from step 310 or 330. Continuing, if a sensor or 2D imaging device is not found in step 350 the software service returns information to the cloud server in step 360 and in step 370 the cloud server communicates to the html web browser user an error or status. If a sensor or 2D dental imaging device was found in step 350, then the client software configures it if required in step 380, arms the sensor for exposure in step 390, and waits to receive an image or error in step 400. If an image is not received or an error has occurred, then the cloud software is notified in step 410 and the cloud software informs the html client user of error or status. If an image is received in step 400, then continuing in step 430; notification is communicated to the cloud software than an image is ready for upload. In step 440 the image is uploaded to the cloud storage and saved. And finally in step 450 the image is made available for display in a standard html web browser located on the client machine.

Utilizing the novel method enables a HTML web browser supporting acquisition from dental imaging devices via using a de-coupled software service operating on a client device. The software service has ability to detect a client connected dental imaging device and supports acquisition from said dental imaging device. The software service used in combination with an application server software has means to detect client operating system and to determine which information can be used for automatic download of necessary drivers, API and software service. The software service allows the ability for any HTML web browser to be compatible and able to direct acquisition of a dental x-ray imaging device on any supported operating system including Windows, OSX, IOS, Linux, or Android and without adding a control, browser extension or plug-in into the standard HTML web browser for controlling or directing acquisition from said dental imaging device. This is accomplished in an automatic or semi-automatic method.

From the foregoing it can be seen that a cloud based 2D dental imaging system with HTML web browser acquisition has been described. It should be noted that the sketches are not drawn to scale and that distances of between the figures are not to be considered significant.

Accordingly it is intended that the foregoing disclosure and showing made in the drawing shall be considered only as an illustration of the principle of the present invention.

What is claimed is:

1. A web browser-based imaging system for acquiring images wherein said web browser-based imaging system comprises:
 a. a plurality of imaging devices, including at least one specific imaging device, located in a dental office;
 b. a client computer having a web browser located in the dental office wherein said web browser operating on client computer does not require using either a web browser add-on extension or web browser plug-in to facilitate communication between the web browser and the separate decoupled imaging software application in order to command the decoupled imaging software application to acquire a new image from said specific imaging device whereby in response to a command to arm said specific imaging device or response to arm any connected imaging device via user input into said web browser which uses software to determine that the user input was for a specific imaging device or any connected imaging device and subsequently issues a command to said client computer operating said decoupled imaging software application to arm an imaging device and which enacts the process of image acquisition in said decoupled imaging software application from that specific imaging device;
 c. a decoupled software application operating upon said client computer wherein said decoupled software application communicates with said specific imaging device and receives a new image from said specific imaging device via the image being acquired and then delivered to the web browser by the separate decoupled imaging software application wherein said decoupled imaging software application receives direction to initiate acquisition of an image or image data via communication from said web browser of said client computer and wherein said web browser does not directly communicate with the specific imaging devices device driver and wherein the decoupled imaging software application is in communication with the device driver interface of said specific imaging device whereby said decoupled software imaging application initializes said specific imaging device and enacts a new image acquisition from said specific imaging device in response to input received from said web browser and whereby said web browser is not using a plug-in to communicate the user input to the decoupled software application; and
 d. a cloud server with dental imaging software installed wherein said client computer with said web browser and said cloud server are connected via an internet connection and wherein said dental imaging software searches for information for said specific imaging device based upon said user input and said dental imaging software returns said information to said client computer regarding availability of device or error conditions of the specific imaging device.

2. A web browser-based imaging system for acquiring images according to claim 1 wherein at least one of said imaging devices is an x-ray sensor.

3. A web browser-based imaging system for acquiring images according to claim 1 wherein said cloud server includes a storage device to receive and store images or image data.

4. A web browser-based imaging system for acquiring images according to claim 1 wherein said decoupled software application receives direction to receive image or image data via communication from either said application server or from said web browser of said client computer.

5. A web browser-based imaging system for acquiring images according to claim 1 wherein said decoupled software application is in communication with the device driver interface of said specific imaging device whereby said decoupled software application initializes said specific imaging device and enacts a new image acquisition.

6. A web browser-based imaging system for acquiring color dental images according to claim 1 wherein said cloud server includes a storage device to receive and store images or image data.

7. A web browser-based imaging system for acquiring color dental images according to claim 6 wherein said decoupled software application receives direction to receive image or image data via communication from either said application server or from said web browser of said client computer.

8. A web browser-based imaging system for acquiring images according to claim 1 wherein at least one of said imaging devices is a color imaging device.

9. A web browser-based imaging system for acquiring color dental images according to claim 8 wherein said color imaging device is a dental camera.

10. A web browser-based imaging system for acquiring x-ray radiographs according to claim 2 wherein said imaging device is a dental x-ray sensor.

* * * * *